(12) United States Patent
Knust et al.

(10) Patent No.: US 8,207,220 B2
(45) Date of Patent: Jun. 26, 2012

(54) SUBSTITUTED BENZOTHIAZOLES AS OREXIN ANTAGONISTS

(75) Inventors: Henner Knust, Rheinfelden (DE); Matthias Nettekoven, Grenzach-Wyhlen (DE); Emmanuel Pinard, Linsdorf (FR); Olivier Roche, Folgensbourg (FR); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/958,440

(22) Filed: Dec. 2, 2010

(65) Prior Publication Data

US 2011/0071154 A1    Mar. 24, 2011

Related U.S. Application Data

(62) Division of application No. 12/506,302, filed on Jul. 21, 2009, now Pat. No. 7,923,470.

(30) Foreign Application Priority Data

Jul. 29, 2008 (EP) .................................... 08161316

(51) Int. Cl.
*A61K 31/38* (2006.01)
(52) U.S. Cl. ......... 514/443; 548/161; 548/206; 548/530
(58) Field of Classification Search ................... 514/443; 548/161, 206, 530
See application file for complete search history.

(56) References Cited

FOREIGN PATENT DOCUMENTS

| WO | 02/090355 | 11/2002 |
| WO | 2009/080533 | 7/2009 |

OTHER PUBLICATIONS

Siegel, Annu. Reb. Psychol. vol. 55, pp. 125-148 (2004).
Delecea et al., Proc. Natl. Acad. Sci. USA vol. 95 pp. 322-327 (1998).
Sakurai et al., Cell vol. 92, pp. 573-585 (1998)..
Sakurai, Regulatory Peptides vol. 126 pp. 3-10 (2005).
Peyron et al., J. Neurosoi. vol. 18, pp. 9996-10015 (1998).
Nambu et al., Brain Res. vol. 827 pp. 243-260 (1999).
Chemelli et al., Cell, vol. 98 pp. 437-451 (1999).
Lin et al., Cell. vol. 98 pp. 365-376 (1999).
Nishino et al., Lancet vol. 355 pp. 39-40 (2000).
Peyron et al., Nature Medicine vol. 6 pp. 991-997 (2000).
Mignot et al., Sleep vol. 11 pp. 1012-1020 (1997).
Piper et al., Eur. J. Neuroscience vol. 12, pp. 726-730 (2000).
Sakamoto et al., Regul. Pept. vol. 118, pp. 183-191 (2004).
Ida et al., Biochem. Biophys. Res. Comm. vol. 270, pp. 318-323 (2000).
Kuru et al., Neuroreport vol. 11 pp. 1977-1980 (2000).
Vvinsky Sommerer et al., J. Neuroscience vol. 24 pp. 11439-11448 (2004).
Suzuki et al., Brain Research vol. 1044, pp. 116-121 (2005).
Digby et al., J. Endocrinol. vol. 191 pp. 129-136 (2006).
Cai, et al., Expert Opin. Ther. Patents vol. 16(5) pp. 631-646 (2006).
Bingham et al., Current Opinion in Drug Discovery & Development vol. 9(5) pp. 551-559 (2006).
Bourgin et al., J. Neurosoi. vol. 20(20) pp. 7760-7765 (2000).
Smith, et al., Neurosci. Lett. vol. 341(3) pp. 256-258 (2003).
Malherbe et al., Mol. Pharmacol. vol. 64 pp. 823-832 (2003).
Yamazaki et al., Bioorganic & Medicinal Chemistry Letters vol. 17 pp. 4689-4693 (2007).
Chang et al., Neurosci. Research vol. 57, Issue 3, pp. 462-466 (2007).

*Primary Examiner* — James O Wilson
*Assistant Examiner* — Douglas M Willis
(74) *Attorney, Agent, or Firm* — George W. Johnston; Patricia S. Rocha-Tramaloni; Kimberly J. Prior

(57) ABSTRACT

The present invention is concerned with novel sulfonamides of formula I

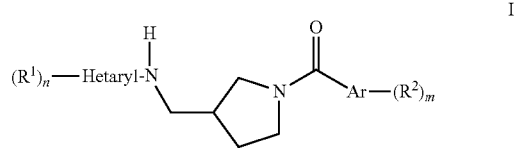

wherein $R^1$, $R^2$, Ar, Hetaryl, m and n are as described in the description and claims. The compounds are orexin receptor antagonists, useful in the treatment of disorders, in which orexin pathways are involved.

8 Claims, No Drawings

SUBSTITUTED BENZOTHIAZOLES AS OREXIN ANTAGONISTS

PRIORITY TO RELATED APPLICATION(S)

This application is a division of U.S. application Ser. No. 12/506,302, filed Jul. 21, 2009, now pending; which claims the benefit of European Patent Application No. 08161316.8, filed Jul. 29, 2008. The entire contents of the above-identified applications are hereby incorporated by reference.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al., *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al., *Cell*, 98, 365-376, 1999), (c) lack of OX-A and OX-B was observed in human narcoleptic patients (Nishino et al., *Lancet*, 355, 39-40, 2000; Peyron et al., *Nature Medicine*, 6, 991-997, 2000), (d) it has been shown that Modafinil, an anti-narcoleptic drug with unknown mechanism of action, activates orexin neurons (Mignot et al., *Sleep*, 11, 1012-1020, 1997; Chemelli et al., *Cell*, 98, 437-451, 1999). The intracerebroventricular (icy) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the orticotrophin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al., *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R(N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., *Neurosci Res.*, 21 Dec. 2006). A recent preclinical report (Suzuki et al., *Brain Research*, 1044, 116-121, 2005) has suggested an anxiogenic effect of OX-A. The icv injection of OX-A caused an anxiety-like behavior in mice. Effects were similar to those of orticotrophin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

Numerous documents describe the current knowledge on orexin pathway, for example the following documents:

Expert Opin. Ther. Patents (2006), 16(5), 631-646
Current Opinion in Drug Discovery & Development, 2006, 9(5), 551-559
J. Neurosci (2000), 20(20), 7760-7765
Neurosci Lett, (2003), 341(3), 256-258

SUMMARY OF THE INVENTION

The present invention provides compounds of formula I

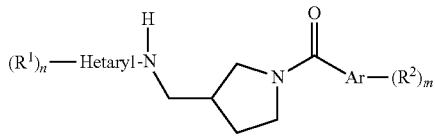

I wherein
R¹ is halogen;
R² is halogen, lower alkyl, lower alkoxy, lower alkyl substituted by halogen, lower alkoxy substituted by halogen or is phenyl;
Hetaryl is

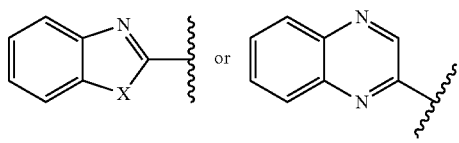

X is O or S;
Ar is aryl or heteroaryl;
n is 0, 1 or 2;
m is 0, 1 or 2;
or to pharmaceutically suitable acid addition salts, optically pure enantiomers, racemates or diastereomeric mixtures thereof.

The invention also provides pharmaceutical compositions containing compounds of the invention and a pharmaceutically acceptable carrier. The invention further provides methods for the manufacture of the compounds and compositions of the invention.

Compounds of formula I are orexin receptor antagonists. Thus, the invention also provides methods for the treatment of disorders, in which orexin pathways are involved like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes a lower alkyl group as defined above, wherein at least one hydrogen atom is replaced by halogen, for example —CF₃, —CHF₂, —CH₂F, —CH₂CF₃, —CF₂CHF₂, —CH₂CH₂CF₃, —CH₂CF₂CF₃ and the like. Preferred lower alkyl substituted by halogen groups are groups having 1-4 carbon atoms.

The term "lower alkoxy" denotes a lower alkyl group as defined above, which is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes a lower alkoxy group as defined above wherein at least one hydrogen atom is replaced by halogen. Preferred lower alkoxy substituted by halogen groups are groups having 1-4 carbon atoms.

The term "halogen" denotes chlorine, iodine, fluorine and bromine.

The term "aryl" denotes an aromatic mono or bicyclic carbon ring system, for example phenyl or naphthyl, preferably phenyl.

The term "heteroaryl" denotes a five-or six membered aromatic ring system, containing one or two heteroatoms, selected from O, S and N, for example isoxazolyl, oxazolyl, imidazolyl, pyridinyl and the like, preferably isoxazolyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those wherein Hetaryl is benzoxazol-2-yl,

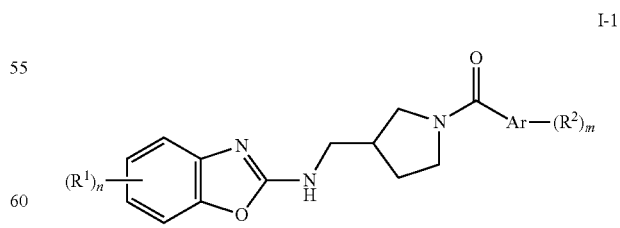

I-1 for example the following examples:
{3-[(6-chloro-benzooxazol-2-ylamino)-methyl]-pyrrolidin-1-yl}-(2,6-dimethoxy-phenyl)-methanone;
{(S)-3-[(6-chloro-benzooxazol-2-ylamino)-methyl]-pyrrolidin-1-yl}-(2,6-dimethoxy-phenyl)-methanone;

{(S)-3-[(6-chloro-benzooxazol-2-ylamino)-methyl]-pyrrolidin-1-yl}-(2-trifluoromethyl-phenyl)-methanone;
{(S)-3-[(6-chloro-benzooxazol-2-ylamino)-methyl]-pyrrolidin-1-yl}-(2-trifluoromethoxy-phenyl)-methanone;
{(S)-3-[(6-chloro-benzooxazol-2-ylamino)-methyl]-pyrrolidin-1-yl}-[2-(1,1,2,2-tetrafluoro-ethoxy)-phenyl]-methanone;
{(S)-3-[(6-chloro-benzooxazol-2-ylamino)-methyl]-pyrrolidin-1-yl}-(5-methyl-2-trifluoromethyl-phenyl)-methanone;
{(S)-3-[(6-chloro-benzooxazol-2-ylamino)-methyl]-pyrrolidin-1-yl}-(5-methyl-3-phenyl-isoxazol-4-yl)-methanone;
{(S)-3-[(6-chloro-benzooxazol-2-ylamino)-methyl]-pyrrolidin-1-yl}-(5-phenyl-isoxazol-4-yl)-methanone;
{(S)-3-[(6-chloro-benzooxazol-2-ylamino)-methyl]-pyrrolidin-1-yl}-(2-chloro-5-methyl-phenyl)-methanone;
{(S)-3-[(6-chloro-benzooxazol-2-ylamino)-methyl]-pyrrolidin-1-yl}-(2-methoxy-5-methyl-phenyl)-methanone;
{(S)-3-[(7-fluoro-benzooxazol-2-ylamino)-methyl]-pyrrolidin-1-yl}-(2-trifluoromethoxy-phenyl)-methanone;
{(S)-3-[(7-fluoro-benzooxazol-2-ylamino)-methyl]-pyrrolidin-1-yl}-[2-(1,1,2,2-tetrafluoro-ethoxy)-phenyl]-methanone;
{(S)-3-[(7-fluoro-benzooxazol-2-ylamino)-methyl]-pyrrolidin-1-yl}-(5-methyl-2-trifluoromethyl-phenyl)-methanone;
{(S)-3-[(7-fluoro-benzooxazol-2-ylamino)-methyl]-pyrrolidin-1-yl}-(5-methyl-3-phenyl-isoxazol-4-yl)-methanone;
{(S)-3-[(7-fluoro-benzooxazol-2-ylamino)-methyl]-pyrrolidin-1-yl}-(5-phenyl-isoxazol-4-yl)-methanone;
(2-chloro-5-methyl-phenyl)-{(S)-3-[(7-fluoro-benzooxazol-2-ylamino)-methyl]-pyrrolidin-1-yl}-methanone; and
{(S)-3-[(7-fluoro-benzooxazol-2-ylamino)-methyl]-pyrrolidin-1-yl}-(2-methoxy-5-methyl-phenyl)-methanone.

Preferred compounds of formula I-1 as defined above are
{3-[(6-Chloro-benzooxazol-2-ylamino)-methyl]-pyrrolidin-1-yl}-(2,6-dimethoxy-phenyl)-methanone;
{(S)-3-[(6-Chloro-benzooxazol-2-ylamino)-methyl]-pyrrolidin-1-yl}-(2,6-dimethoxy-phenyl)-methanone;
{(S)-3-[(6-Chloro-benzooxazol-2-ylamino)-methyl]-pyrrolidin-1-yl}-(5-methyl-3-phenyl-isoxazol-4-yl)-methanone; and
{(S)-3-[(7-Fluoro-benzooxazol-2-ylamino)-methyl]-pyrrolidin-1-yl}-(5-methyl-3-phenyl-isoxazol-4-yl)-methanone.

Preferred compounds of formula I are further those wherein Hetaryl is benzthiazol-2-yl,

I-2

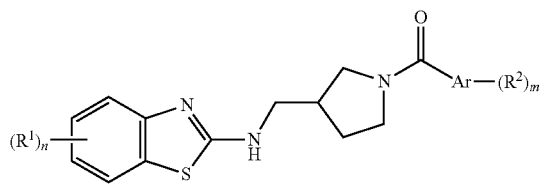

for example the following examples:
{(S)-3-[(6-fluoro-benzothiazol-2-ylamino)-methyl]-pyrrolidin-1-yl}-(2-trifluoromethyl-phenyl)-methanone;
{(S)-3-[(6-fluoro-benzothiazol-2-ylamino)-methyl]-pyrrolidin-1-yl}-(2-trifluoromethoxy-phenyl)-methanone;
{(S)-3-[(6-fluoro-benzothiazol-2-ylamino)-methyl]-pyrrolidin-1-yl}-[2-(1,1,2,2-tetrafluoro-ethoxy)-phenyl]-methanone;
{(S)-3-[(6-fluoro-benzothiazol-2-ylamino)-methyl]-pyrrolidin-1-yl}-(5-methyl-2-trifluoromethyl-phenyl)-methanone;
{(S)-3-[(6-fluoro-benzothiazol-2-ylamino)-methyl]-pyrrolidin-1-yl}-(5-methyl-3-phenyl-isoxazol-4-yl)-methanone;
{(S)-3-[(6-fluoro-benzothiazol-2-ylamino)-methyl]-pyrrolidin-1-yl}-(5-phenyl-isoxazol-4-yl)-methanone;
(2-chloro-5-methyl-phenyl)-{(S)-3-[(6-fluoro-benzothiazol-2-ylamino)-methyl]-pyrrolidin-1-yl}-methanone; and
{(S)-3-[(6-fluoro-benzothiazol-2-ylamino)-methyl]-pyrrolidin-1-yl}-(2-methoxy-5-methyl-phenyl)-methanone.

Preferred compounds of formula I-2 as defined above are
{(S)-3-[(6-Fluoro-benzothiazol-2-ylamino)-methyl]-pyrrolidin-1-yl}-[2-(1,1,2,2-tetrafluoro-ethoxy)-phenyl]-methanone;
{(S)-3-[(6-Fluoro-benzothiazol-2-ylamino)-methyl]-pyrrolidin-1-yl}-(5-methyl-3-phenyl-isoxazol-4-yl)-methanone; and
{(S)-3-[(6-Fluoro-benzothiazol-2-ylamino)-methyl]-pyrrolidin-1-yl}-(5-phenyl-isoxazol-4-yl)-methanone.

Preferred compounds of formula I are further those wherein Hetaryl is quinoxalin-2-yl,

I-3 for example the following examples:
{(S)-3-[(6-chloro-quinoxalin-2-ylamino)-methyl]-pyrrolidin-1-yl}-(2-trifluoromethoxy-phenyl)-methanone;
{(S)-3-[(6-chloro-quinoxalin-2-ylamino)-methyl]-pyrrolidin-1-yl}-[2-(1,1,2,2-tetrafluoro-ethoxy)-phenyl]-methanone;
{(S)-3-[(6-chloro-quinoxalin-2-ylamino)-methyl]-pyrrolidin-1-yl}-(5-methyl-2-trifluoromethyl-phenyl)-methanone;
{(S)-3-[(6-chloro-quinoxalin-2-ylamino)-methyl]-pyrrolidin-1-yl}-(5-methyl-3-phenyl-isoxazol-4-yl)-methanone;
{(S)-3-[(6-chloro-quinoxalin-2-ylamino)-methyl]-pyrrolidin-1-yl}-(5-phenyl-isoxazol-4-yl)-methanone;
(2-chloro-5-methyl-phenyl)-{(S)-3-[(6-chloro-quinoxalin-2-ylamino)-methyl]-pyrrolidin-1-yl}-methanone; and
{(S)-3-[(6-chloro-quinoxalin-2-ylamino)-methyl]-pyrrolidin-1-yl}-(2-methoxy-5-methyl-phenyl)-methanone.

A preferred compound of formula I-3 as defined above is
{(S)-3-[(6-Chloro-quinoxalin-2-ylamino)-methyl]-pyrrolidin-1-yl}-[2-(1,1,2,2-tetrafluoro-ethoxy)-phenyl]-methanone.

Preferred compounds as defined above are those, wherein $R^1$ is Cl or F. Other preferred compounds as defined above are those, wherein n is 1.

Other preferred compounds as defined above are those, wherein $R^2$ is lower alkyl, lower alkoxy, lower alkoxy substituted by halogen or phenyl, particularly wherein $R^2$ is methyl, methoxy, 1,1,2,2-tetrafluoro-ethoxy or phenyl.

Preferably, m is 1 or 2. Other preferred compounds as define above are those, wherein Ar is phenyl or isoxazolyl.

The present compounds of formula I and their pharmaceutically acceptable salts can be prepared by methods known in the art, for example, by processes described below, which process comprises a) reacting a compound of formula

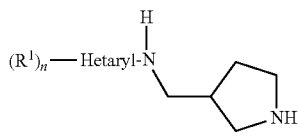

IV with a compound of formula

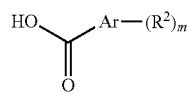

V or with the corresponding acid chloride thereof to obtain a compound of formula

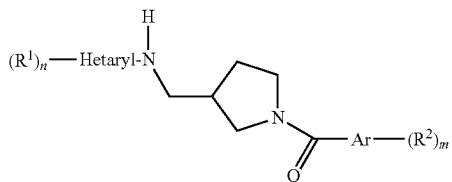

I wherein R', $R^2$, Ar, Hetaryl, m and n are as defined above, and if desired, converting the compounds obtained into pharmaceutically acceptable acid addition salts.

General Experimental Part

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

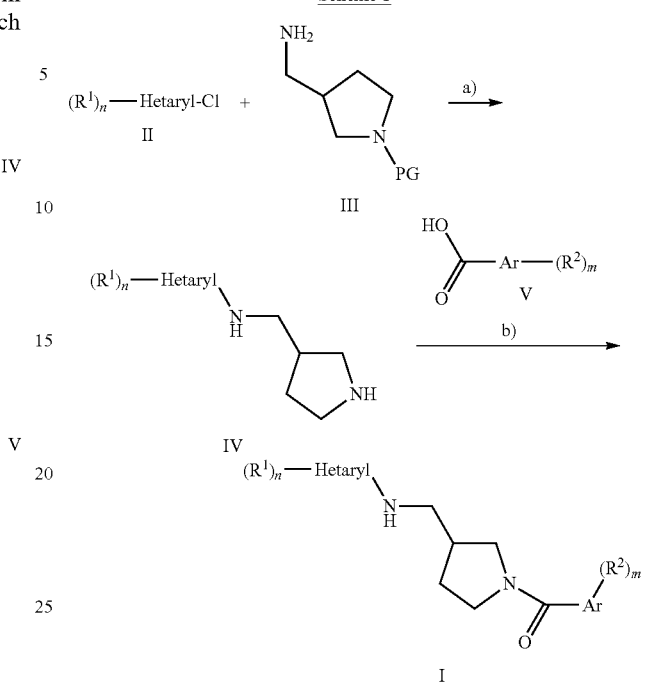

Step a)

Aromatic heterocyclic compounds II are either commercially available or can be synthesized according to procedures described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999), for instance from their respective HET-OH derivatives. Protected amino-methylpyrrolidines III are commercially available or can be synthesized according to procedures described in literature. Protected amino-methylpyrrolidines III can be reacted with II in the presence or absence of a solvent and the presence or the absence of a base. There is no particular restriction on the nature of the solvent to be employed, provided that it has no adverse effect on the reaction or the reagents involved and that it can dissolve the reagents, at least to some extent. Examples for suitable solvents include dichloromethane (DCM), dimethylformamide (DMF), tetrahydrofuran (THF) and the like. There is no particular restriction on the nature of the base used in this stage, and any base commonly used in this type of reaction may equally be employed here. Examples of such bases include $NEt_3$, DIPEA and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the protected intermediate (convenient PG=Boc) which can be subjected to acidic cleavage of the protecting group in the presence of a solvent. There is no particular restriction on the nature of the solvent to be employed, provided that it has no adverse effect on the reaction or the reagents involved and that it can dissolve the reagents, at least to some extent. Examples for suitable solvents include dichloromethane (DCM), dioxane, tetrahydrofuran (THF) and the like. There is no particular restriction on the nature of the acid used in this stage, and any acid commonly used in this type of reaction may equally be employed here. Examples of such acid include HCl and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield aminomethyl-pyrrolidine derivatives IV.

Step b)

Transformation of intermediate aminomethyl-pyrrolidine derivatives IV with acids (under coupling conditions with a coupling agent) or acid chlorides V is well know in the art. For analogous examples in literature refer to Comprehensive Organic Transformations: A Guide to Functional Group Preparations, 2nd Edition, Richard C. Larock. John Wiley & Sons, New York, N.Y. 1999. However, we find it convenient to react intermediate aminomethyl-pyrrolidine derivatives IV with acid chlorides in the presence or absence of a base and the presence or absence of a solvent. There is no particular restriction on the nature of the solvent to be employed, provided that it has no adverse effect on the reaction or the reagents involved and that it can dissolve the reagents, at least to some extent. Examples for suitable solvents include dichloromethane (DCM), dimethylformamide (DMF), tetrahydrofuran (THF) and the like. There is no particular restriction on the nature of the base used in this stage, and any base commonly used in this type of reaction may equally be employed here. Examples of such bases include pyridine, $NEt_3$, DIPEA and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield aminomethyl-pyrrolidine derivatives I.

The compounds were investigated in accordance with the test given hereinafter.

Intracellular $Ca^{2+}$ Mobilization Assay

The Chinese Hamster Ovary (dHFr-) mutant cell line stably expressing human orexin-1 (hOX1) or human orexin-2 (hOX2) receptors were maintained in Dulbecco's Modified Eagle Medium (1×) with GlutaMax™1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 µg/ml penicillin and 100 µg/ml streptomycin. The cells were seeded at $5×10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 µM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., *Mol. Pharmacol.*, 64, 823-832, 2003). Orexin A (catalog No. 1455, Toris Cookson Ltd, Bristol, UK) was used as agonist. Orexin A (50 mM stock solution in DMSO) was diluted in FLIPR buffer+0.1% BSA. The $EC_{50}$ and $EC_{80}$ values of orexin-A were measured daily from standard agonist concentration-response curves in CHO(dHFr-)-OX1R and -OX2R cell lines. All compounds were dissolved in 100% DMSO. Inhibition curves were determined by addition of 11 concentrations (0.0001-10 µM) of inhibitory compounds and using $EC_{80}$ value of orexin-A as agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{nH})$, where $n_H$=slope factor using Excel-fit 4 software (Microsoft). $K_b$ values were calculated according to the following equation $K_b=IC_{50}/(1+[A]/EC_{50})$ where A is the concentration of agonist added which is very close to agonist $EC_{80}$ value, and $IC_{50}$ and EC50 values were derived from the antagonist inhibition and orexin-A or B agonist curves, respectively.

The compounds show a $K_b$ value in human on orexin receptor as shown in the table below.

| Example | $K_b$ (µM) OX2R (human) | Example | $K_b$ (µM) OX2R (human) | Example | $K_b$ (µM) OX2R (human) |
|---|---|---|---|---|---|
| 1 | 0.0292 | 12 | 0.214 | 23 | 0.1225 |
| 2 | 0.0573 | 13 | 0.1491 | 24 | 0.7543 |
| 3 | 0.2068 | 14 | 0.3038 | 25 | 0.6749 |
| 4 | 0.1292 | 15 | 0.0819 | 26 | 0.1777 |
| 5 | 0.0318 | 16 | 0.1473 | 27 | 0.0839 |
| 6 | 0.115 | 17 | 0.565 | 28 | 0.3306 |
| 7 | 0.0623 | 18 | 0.3552 | 29 | 0.4067 |
| 8 | 0.0829 | 19 | 0.6896 | 30 | 0.3398 |
| 9 | 0.3367 | 20 | 0.0772 | 31 | 0.539 |
| 10 | 0.1653 | 21 | 0.3962 | 32 | 0.1846 |
| 11 | 0.7255 | 22 | 0.0566 | | |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The invention also provides methods for the therapeutic and/or prophylactic treatment of sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain or irritable bowel syndrome, which method comprises administering a compound as defined above to a human being or animal.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction. More preferred indications are sleep disorders, particularly sleep apnea, narcolepsy, insomnia, parasomnia, jet lag syndrome and sleep disorders associated with neurological diseases.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/ tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Experimental Part:

EXAMPLE 1

{3-[(6-Chloro-benzooxazol-2-ylamino)-methyl]-pyrrolidin-1-yl}-(2,6-dimethoxy-phenyl)-methanone

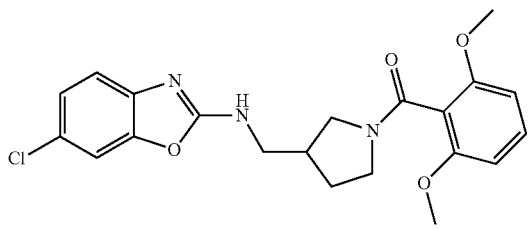

a) Step 1:

3-[(6-Chloro-benzooxazol-2-ylamino)-methyl]-pyrrolidine-1-carboxylic acid tert-butyl ester

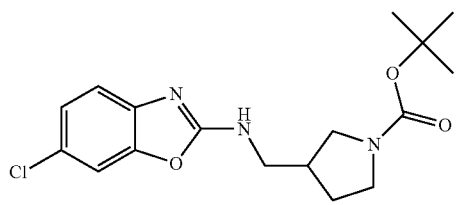

A mixture of 220 mg (1.1 mmol) 3-aminomethyl-pyrrolidine-1-carboxylic acid tert-butyl ester (commercially available), 188 mg (1 mmol) 2,6-dichloro-benzooxazole (commercially available) and 303 mg (3 mmol) NEt₃ in 4 mL DCM was stirred at room temperature over night. After evaporation to dryness the residue was purified with flash column chromatography on silica eluting with a gradient formed from ethyl acetate and heptane. The product containing fractions were evaporated to yield 351 mg (99%) of the title compound. MS (m/e): 352.4 (MH⁺).

b) Step 2:

(6-Chloro-benzooxazol-2-yl)-pyrrolidin-3-ylmethyl-amine; hydrochloride

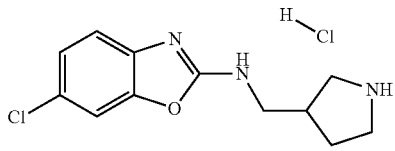

A mixture of 350.2 mg (0.99 mmol) 3-[(6-Chloro-benzooxazol-2-ylamino)-methyl]-pyrrolidine-1-carboxylic acid tert-butyl ester and 3 mL 4N HCl in dioxane was stirred at room temperature over night. The mixture was decanted and the residue evaporated to dryness to yield the title compound which was used in the consecutive step without further purification. MS (m/e): 252.2 (MH⁺).

c) Step 3:

{3-[(6-Chloro-benzooxazol-2-ylamino)-methyl]-pyrrolidin-1-yl}-(2,6-dimethoxy-phenyl)-methanone A mixture of 20 mg (0.07 mmol) (6-chloro-benzooxazol-2-yl)-pyrrolidin-3-ylmethyl-amine; hydrochloride, 15 mg (0.77 mmol) 2,6-dimethoxybenzoyl chloride and 10 mg (0.1 mmol) NEt₃ in 2 mL DCM was shaken at room temperature over night. After evaporation the residue was subjected to purification by preparative HPLC on reversed phase eluting with a gradient formed from acetonitrile, water and formic acid. The product containing fractions were evaporated to yield 6.5 mg (22%) of the title compound. MS (m/e): 416.2 (MH⁺).

INTERMEDIATE 1

(6-Chloro-benzooxazol-2-yl)-(R)-1-pyrrolidin-3-ylmethyl-amine, hydrochloride

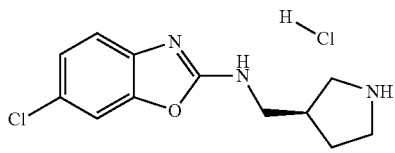

In analogy to the procedure described for the synthesis of (6-Chloro-benzooxazol-2-yl)-pyrrolidin-3-ylmethyl-amine; hydrochloride (example 1, step 2) the title compound was prepared from (S)-3-aminomethyl-pyrrolidine-1-carboxylic acid tert-butyl ester and 2,6-dichloro-benzooxazole (commercially available) and subsequent cleavage of the tert-butyloxy carbonyl-protecting group through treatment with HCl in dioxane. MS (m/e): 252.2 (MH⁺).

INTERMEDIATE 2

(6-Fluoro-benzothiazol-2-yl)-(R)-1-pyrrolidin-3-ylmethyl-amine, hydrochloride

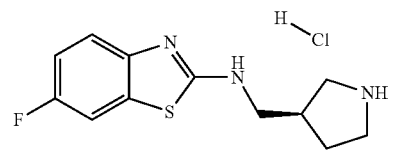

In analogy to the procedure described for the synthesis of (6-Chloro-benzooxazol-2-yl)-pyrrolidin-3-ylmethyl-amine; hydrochloride (example 1, step 2) the title compound was prepared from (S)-3-aminomethyl-pyrrolidine-1-carboxylic acid tert-butyl ester and 2-chloro-6-fluoro-benzothiazole (commercially available) and subsequent cleavage of the tert-butyloxy carbonyl-protecting group through treatment with HCl in dioxane. MS (m/e): 252.1 (MH⁺).

INTERMEDIATE 3

(7-Fluoro-benzooxazol-2-yl)-(R)-1-pyrrolidin-3-ylmethyl-amine, hydrochloride

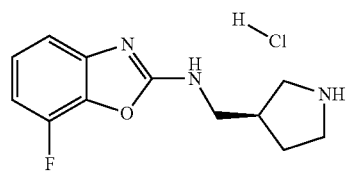

In analogy to the procedure described for the synthesis of (6-Chloro-benzooxazol-2-yl)-pyrrolidin-3-ylmethyl-amine; hydrochloride (example 1, step 2) the title compound was prepared from (S)-3-aminomethyl-pyrrolidine-1-carboxylic acid tert-butyl ester and 2-chloro-7-fluoro-benzooxazole (Bioorganic & Medicinal Chemistry Letters 2007, 17, 4689) and subsequent cleavage of the tert-butyloxy carbonyl-protecting group through treatment with HCl in dioxane. MS (m/e): 236.1 (MH⁺).

INTERMEDIATE 4

(6-Chloro-quinoxalin-2-yl)-(R)-1-pyrrolidin-3-ylmethyl-amine

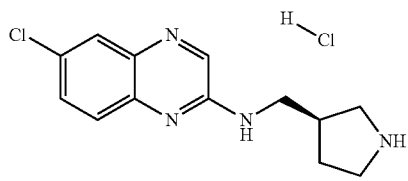

In analogy to the procedure described for the synthesis of (6-Chloro-benzooxazol-2-yl)-pyrrolidin-3-ylmethyl-amine; hydrochloride (example 1, step 2) the title compound was prepared from (S)-3-aminomethyl-pyrrolidine-1-carboxylic acid tert-butyl ester and 2,6-dichloro-quinoxaline (commercially available) and subsequent cleavage of the tert-butyloxy carbonyl-protecting group through treatment with HCl in dioxane. MS (m/e): 263.1 (MH⁺).

EXAMPLE 2

{(S)-3-[(6-Chloro-benzooxazol-2-ylamino)-methyl]-pyrrolidin-1-yl}-(2,6-dimethoxy-phenyl)-methanone

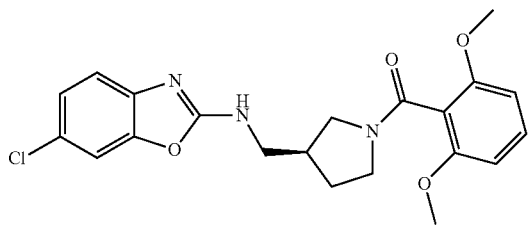

A mixture of 146.3 mg (0.45 mmol) (6-chloro-benzooxazol-2-yl)-(R)-1-pyrrolidin-3-ylmethyl-amine, hydrochloride (intermediate 1), 106.7 mg (0.586 mmol) 2,6-dimethoxy-benzoic acid (commercially available) and 206.9 mg (0.64 mmol) TBTU in 4 mL DMF and 0.3 mL DIPEA was shaken at room temperature over night. The mixture was acidified with formic acid and subjected to purification by preparative HPLC on reversed phase eluting with a gradient formed from acetonitrile, water and formic acid. The product containing fractions were evaporated to yield 72 mg (38%) of the title compound. MS (m/e): 416.2 (MH⁺).

In analogy to the procedure described for the synthesis of {(S)-3-[(6-chloro-benzooxazol-2-ylamino)-methyl]-pyrrolidin-1-yl}-(2,6-dimethoxy-phenyl)-methanone (example 2) further pyrrolidin-3-ylmethyl-amine derivatives have been synthesized from their respective starting materials as mentioned in table 1. Table 1 comprises example 3-example 32.

TABLE 1

| | structure | systematic name | starting materials | MW found MH+ |
|---|---|---|---|---|
| 1 | 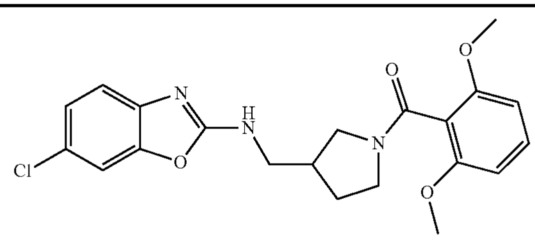 | {3-[(6-Chloro-benzooxazol-2-ylamino)-methyl]-pyrrolidin-1-yl}-(2,6-dimethoxy-phenyl)-methanone | (6-chloro-benzooxazol-2-yl)-pyrrolidin-3-ylmethyl-amine; hydrochloride and 2,6-dimethoxybenzoyl chloride | 416.2 |
| 2 | 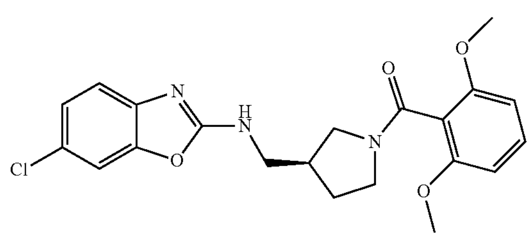 | {(S)-3-[(6-Chloro-benzooxazol-2-ylamino)-methyl]-pyrrolidin-1-yl}-(2,6-dimethoxy-phenyl)-methanone | (6-chloro-benzooxazol-2-yl)-(R)-1-pyrrolidin-3-ylmethyl-amine, hydrochloride (intermediate 1), and 2,6-dimethoxy-benzoic acid | 416.2 |

TABLE 1-continued

| # | structure | systematic name | starting materials | MW found MH+ |
|---|---|---|---|---|
| 3 | 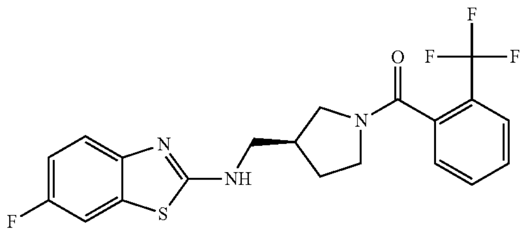 | {(S)-3-[(6-Fluoro-benzothiazol-2-ylamino)-methyl]-pyrrolidin-1-yl}-(2-trifluoromethyl-phenyl)-methanone | (6-Fluoro-benzothiazol-2-yl)-(R)-1-pyrrolidin-3-ylmethyl-amine, hydrochloride (intermediate 2) and 2-trifluoromethyl-benzoic acid (commercially available) | 424.2 |
| 4 | 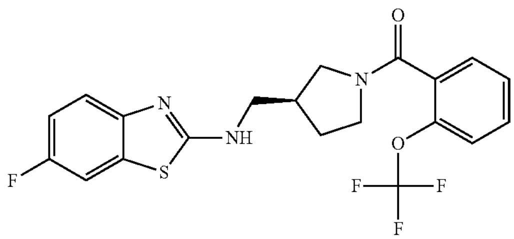 | {(S)-3-[(6-Fluoro-benzothiazol-2-ylamino)-methyl]-pyrrolidin-1-yl}-(2-trifluoromethoxy-phenyl)-methanone | (6-Fluoro-benzothiazol-2-yl)-(R)-1-pyrrolidin-3-ylmethyl-amine, hydrochloride (intermediate 2) and 2-trifluoromethoxy-benzoic acid (commercially available) | 440.2 |
| 5 | 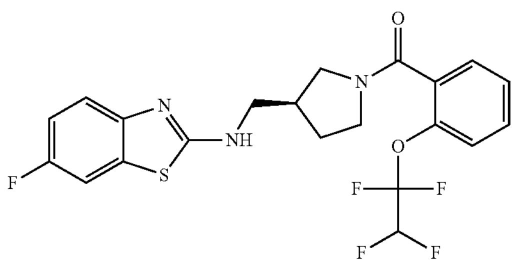 | {(S)-3-[(6-Fluoro-benzothiazol-2-ylamino)-methyl]-pyrrolidin-1-yl}-[2-(1,1,2,2-tetrafluoro-ethoxy)-phenyl]-methanone | (6-Fluoro-benzothiazol-2-yl)-(R)-1-pyrrolidin-3-ylmethyl-amine, hydrochloride (intermediate 2) and 2-(1,1,2,2-tetrafluoro-ethoxy)-benzoic acid (commercially available) | 472.2 |
| 6 | 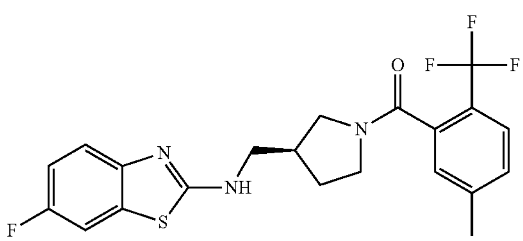 | {(S)-3-[(6-Fluoro-benzothiazol-2-ylamino)-methyl]-pyrrolidin-1-yl}-(5-methyl-2-trifluoromethyl-phenyl)-methanone | (6-Fluoro-benzothiazol-2-yl)-(R)-1-pyrrolidin-3-ylmethyl-amine, hydrochloride (intermediate 2) and 5-methyl-2-trifluoromethyl-benzoic acid (commercially available) | 438.2 |
| 7 | 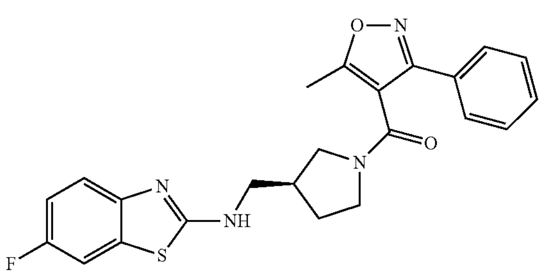 | {(S)-3-[(6-Fluoro benzothiazol-2-ylamino)-methyl]-pyrrolidin-1-yl}-(5-methyl-3-phenyl-isoxazol-4-yl)-methanone | (6-Fluoro-benzothiazol-2-yl)-(R)-1-pyrrolidin-3-ylmethyl-amine, hydrochloride (intermediate 2) and 5-methyl-4-phenyl-isoxazole-3-carboxylic acid (commercially available) | 437.2 |
| 8 | 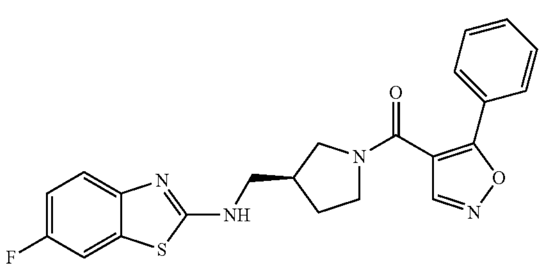 | {(S)-3-[(6-Fluoro-benzothiazol-2-ylamino)-methyl]-pyrrolidin-1-yl}-(5-phenyl-isoxazol-4-yl)-methanone | (6-Fluoro-benzothiazol-2-yl)-(R)-1-pyrrolidin-3-ylmethyl-amine, hydrochloride (intermediate 2) and 4-phenyl-isoxazole-5-carboxylic acid (commercially available) | 423.2 |

TABLE 1-continued

| | structure | systematic name | starting materials | MW found MH+ |
|---|---|---|---|---|
| 9 | 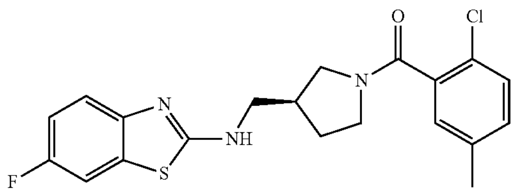 | (2-Chloro-5-methyl-phenyl)-{(S)-3-[(6-fluoro-benzothiazol-2-ylamino)-methyl]-pyrrolidin-1-yl}-methanone | (6-Fluoro-benzothiazol-2-yl)-(R)-1-pyrrolidin-3-ylmethyl-amine, hydrochloride (intermediate 2) and 2-chloro-5-methyl-benzoic acid (commercially available) | 404.2 |
| 10 | 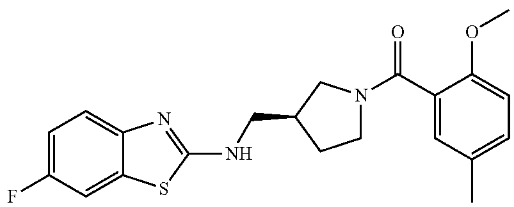 | {(S)-3-[(6-Fluoro-benzothiazol-2-ylamino)-methyl]-pyrrolidin-1-yl}-(2-methoxy-5-methyl-phenyl)-methanone | (6-Fluoro-benzothiazol-2-yl)-(R)-1-pyrrolidin-3-ylmethyl-amine, hydrochloride (intermediate 2) and 2-methoxy-5-methyl-benzoic acid (commercially available) | 400.2 |
| 11 | 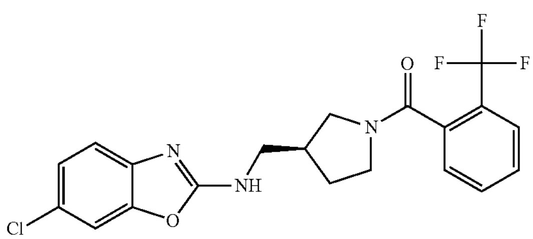 | {(S)-3-[(6-Chloro-benzooxazol-2-ylamino)-methyl]-pyrrolidin-1-yl}-(2-trifluoromethyl-phenyl)-methanone | (6-Chloro-benzooxazol-2-yl)-(R)-1-pyrrolidin-3-ylmethyl-amine, hydrochloride (intermediate 1) and 2-trifluoromethyl-benzoic acid (commercially available) | 424.2 |
| 12 | 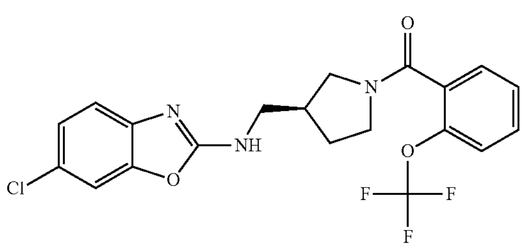 | {(S)-3-[(6-Chloro-benzooxazol-2-ylamino)-methyl]-pyrrolidin-1-yl}-(2-trifluoromethoxy-phenyl)-methanone | (6-Chloro-benzooxazol-2-yl)-(R)-1-pyrrolidin-3-ylmethyl-amine, hydrochloride (intermediate 1) and 2-trifluoromethoxy-benzoic acid (commercially available) | 440.2 |
| 13 | 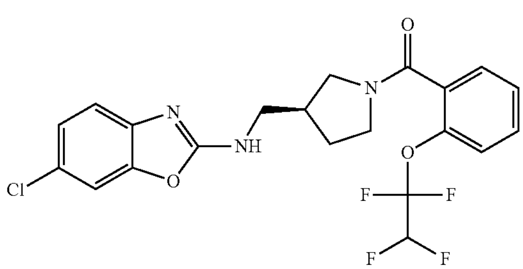 | {(S)-3-[(6-Chloro-benzooxazol-2-ylamino)-methyl]-pyrrolidin-1-yl}-[2-(1,1,2,2-tetrafluoro-ethoxy)-phenyl]-methanone | (6-Chloro-benzooxazol-2-yl)-(R)-1-pyrrolidin-3-ylmethyl-amine, hydrochloride (intermediate 1) and 2-(1,1,2,2-tetrafluoro-ethoxy)-benzoic acid (commercially available) | 472.2 |
| 14 | 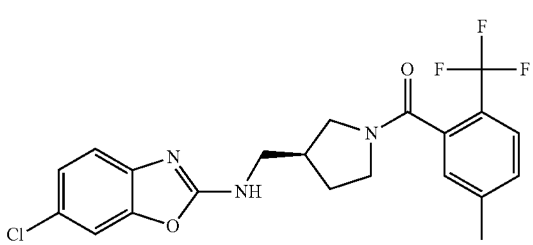 | {(S)-3-[(6-Chloro-benzooxazol-2-ylamino)-methyl]-pyrrolidin-1-yl}-(5-methyl-2-trifluoromethyl-phenyl)-methanone | (6-Chloro-benzooxazol-2-yl)-(R)-1-pyrrolidin-3-ylmethyl-amine, hydrochloride (intermediate 1) and 5-methyl-2-trifluoromethyl-benzoic acid (commercially available) | 438.2 |

TABLE 1-continued

| | structure | systematic name | starting materials | MW found MH+ |
|---|---|---|---|---|
| 15 | 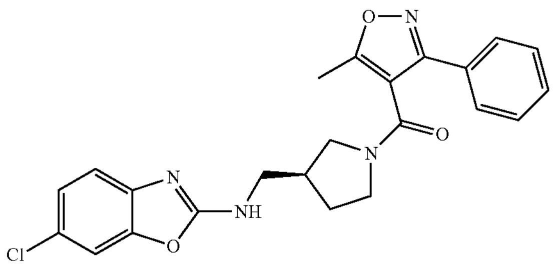 | {(S)-3-[(6-Chloro-benzooxazol-2-ylamino)-methyl]-pyrrolidin-1-yl}-(5-methyl-3-phenyl-isoxazol-4-yl)-methanone | (6-Chloro-benzooxazol-2-yl)-(R)-1-pyrrolidin-3-ylmethyl-amine, hydrochloride (intermediate 1) and 5-methyl-4-phenyl-isoxazole-3-carboxylic acid (commercially available) | 437.2 |
| 16 | 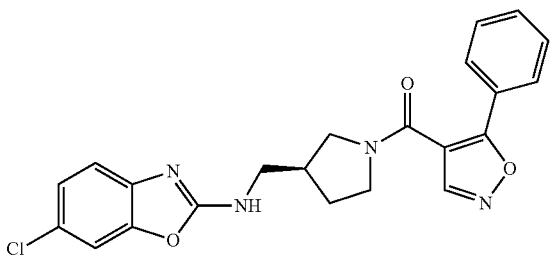 | {(S)-3-[(6-Chloro-benzooxazol-2-ylamino)-methyl)-pyrrolidin-1-yl}-(5-phenyl-isoxazol-4-yl)-methanone | (6-Chloro-benzooxazol-2-yl)-(R)-1-pyrrolidin-3-ylmethyl-amine, hydrochloride (intermediate 1) and 5-methyl-4-phenyl-isoxazole-3-carboxylic acid (commercially available) | 423.2 |
| 17 | 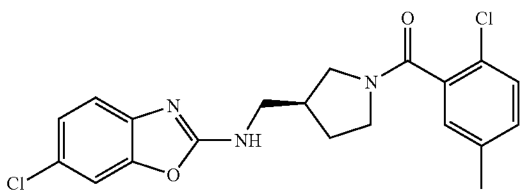 | {(S)-3-[(6-Chloro-benzooxazol-2-ylamino)-methyl]-pyrrolidin-1-yl}-(2-chloro-5-methyl-phenyl)-methanone | (6-Chloro-benzooxazol-2-yl)-(R)-1-pyrrolidin-3-ylmethyl-amine, hydrochloride (intermediate 1) and 2-chloro-5-methyl-benzoic acid (commercially available) | 404.2 |
| 18 | 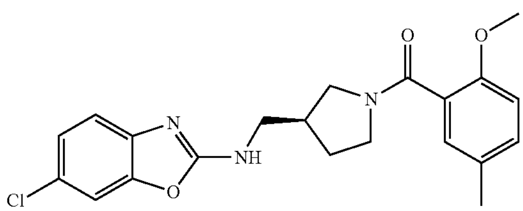 | {(S)-3-[(6-Chloro-benzooxazol-2-ylamino)-methyl]-pyrrolidin-1-yl}-(2-methoxy-5-methyl-phenyl)-methanone | (6-Chloro-benzooxazol-2-yl)-(R)-1-pyrrolidin-3-ylmethyl-amine, hydrochloride (intermediate 1) and 2-methoxy-5-methyl-benzoic acid (commercially available) | 400.2 |
| 19 | 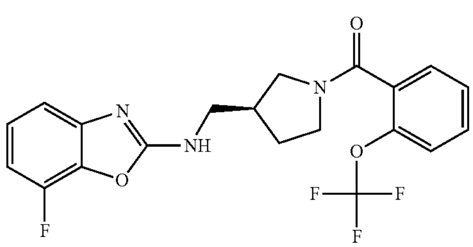 | {(S)-3-[(7-Fluoro-benzooxazol-2-ylamino)-methyl]-pyrrolidin-1-yl}-(2-trifluoromethoxy-phenyl)-methanone | (7-Fluoro-benzooxazol-2-yl)-(R)-1-pyrrolidin-3-ylmethyl-amine, hydrochloride (intermediate 3) and 2-trifluoromethyl-benzoic acid (commercially available) | 424.2 |
| 20 | 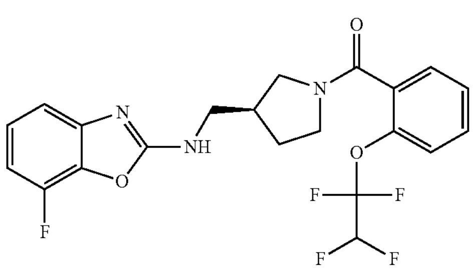 | {(S)-3-[(7-Fluoro-benzooxazol-2-ylamino)-methyl]-pyrrolidin-1-yl}-[2-(1,1,2,2-tetrafluoro-ethoxy)-phenyl]-methanone | (7-Fluoro-benzooxazol-2-yl)-(R)-1-pyrrolidin-3-ylmethyl-amine, hydrochloride (intermediate 3) and 2-(1,1,2,2-tetrafluoro-ethoxy)-benzoic acid (commercially available) | 456.2 |

TABLE 1-continued

| | structure | systematic name | starting materials | MW found MH+ |
|---|---|---|---|---|
| 21 | 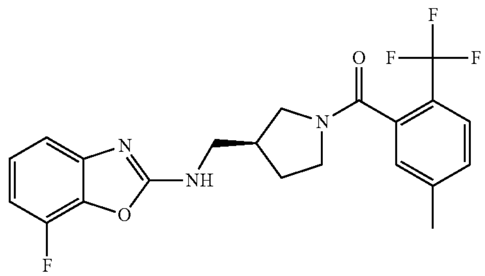 | {(S)-3-[(7-Fluoro-benzooxazol-2-ylamino)-methyl]-pyrrolidin-1-yl}-(5-methyl-2-trifluoromethyl-phenyl)-methanone | (7-Fluoro-benzooxazol-2-yl)-(R)-1-pyrrolidin-3-ylmethyl-amine, hydrochloride (intermediate 3) and 5-methyl-2-trifluoromethyl-benzoic acid (commercially available) | 422.2 |
| 22 | 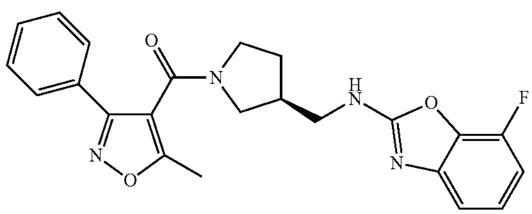 | {(S)-3-[(7-Fluoro-benzooxazol-2-ylamino)-methyl]-pyrrolidin-1-yl}-(5-methyl-3-phenyl-isoxazol-4-yl)-methanone | (7-Fluoro-benzooxazol-2-yl)-(R)-1-pyrrolidin-3-ylmethyl-amine, hydrochloride (intermediate 3) and 5-methyl-4-phenyl-isoxazole-3-carboxylic acid (commercially available) | 421.2 |
| 23 | 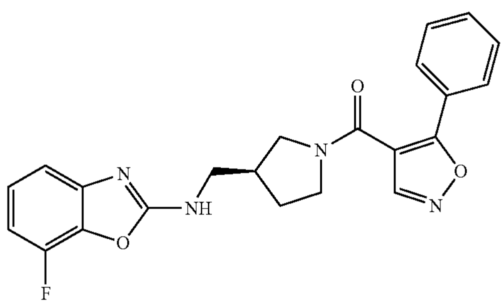 | {(S)-3-[(7-Fluoro-benzooxazol-2-ylamino)-methyl]-pyrrolidin-1-yl}-(5-phenyl-isoxazol-4-yl)-methanone | (7-Fluoro-benzooxazol-2-yl)-(R)-1-pyrrolidin-3-ylmethyl-amine, hydrochloride (intermediate 3) and 4-phenyl-isoxazole-5-carboxylic acid (commercially available) | 407.2 |
| 24 | 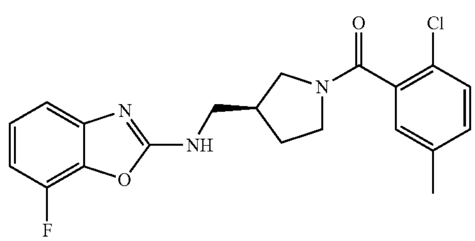 | (2-Chloro-5-methyl-phenyl)-{(S)-3-[(7-fluoro-benzooxazol-2-ylamino)-methyl]-pyrrolidin-1-yl}-methanone | (7-Fluoro-benzooxazol-2-yl)-(R)-1-pyrrolidin-3-ylmethyl-amine, hydrochloride (intermediate 3) and 2-chloro-5-methyl-benzoic acid (commercially available) | 388.2 |
| 25 | 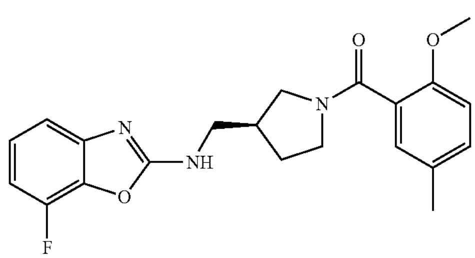 | {(S)-3-[(7-Fluoro-benzooxazol-2-ylamino)-methyl]-pyrrolidin-1-yl}-(2-methoxy-5-methyl-phenyl)-methanone | (7-Fluoro-benzooxazol-2-yl)-(R)-1-pyrrolidin-3-ylmethyl-amine, hydrochloride (intermediate 3) and 2-methoxy-5-methyl-benzoic acid (commercially available) | 384.2 |
| 26 | 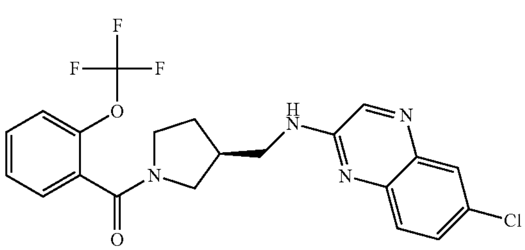 | {(S)-3-[(6-Chloro-quinoxalin-2-ylamino)-methyl]-pyrrolidin-1-yl}-(2-trifluoromethoxy-phenyl)-methanone | (6-Chloro-quinoxalin-2-yl)-(R)-1-pyrrolidin-3-ylmethyl-amine (intermediate 4) and 2-trifluoromethyl-benzoic acid (commercially available) | 451.2 |

TABLE 1-continued

| | structure | systematic name | starting materials | MW found MH+ |
|---|---|---|---|---|
| 27 | 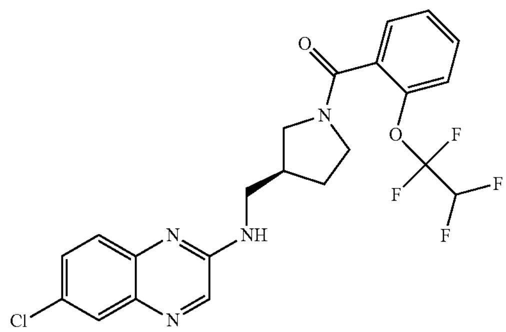 | {(S)-3-[(6-Chloro-quinoxalin-2-ylamino)-methyl]-pyrrolidin-1-yl}-[2-(1,1,2,2-tetrafluoro-ethoxy)-phenyl]-methanone | (6-Chloro-quinoxalin-2-yl)-(R)-1-pyrrolidin-3-ylmethyl-amine (intermediate 4) and 2-(1,1,2,2-tetrafluoro-ethoxy)-benzoic acid (commercially available) | 483.2 |
| 28 | 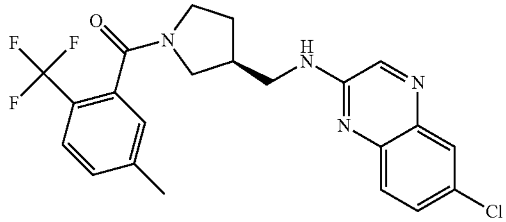 | {(S)-3-[(6-Chloro-quinoxalin-2-ylamino)-methyl]-pyrrolidin-1-yl}-(5-methyl-2-trifluoromethyl-phenyl)-methanone | (6-Chloro-quinoxalin-2-yl)-(R)-1-pyrrolidin-3-ylmethyl-amine (intermediate 4) and 5-methyl-2-trifluoromethyl-benzoic acid (commercially available) | 449.2 |
| 29 | 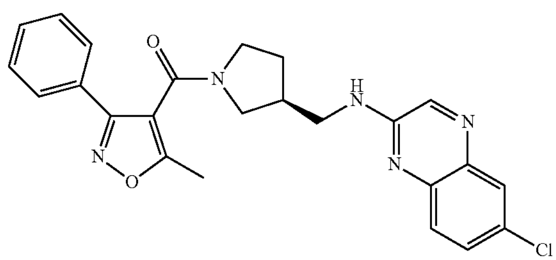 | {(S)-3-[(6-Chloro-quinoxalin-2-ylamino)-methyl]-pyrrolidin-1-yl}-(5-methyl-3-phenyl-isoxazol-4-yl)-methanone | (6-Chloro-quinoxalin-2-yl)-(R)-1-pyrrolidin-3-ylmethyl-amine (intermediate 4) and 5-methyl-4-phenyl-isoxazole-3-carboxylic acid (commercially available) | 448.3 |
| 30 | 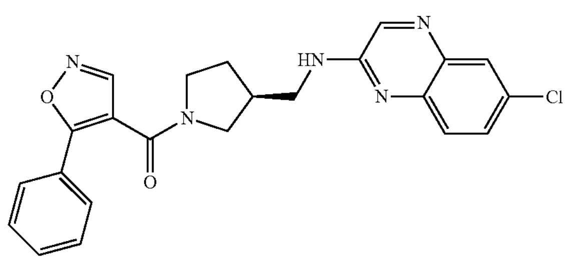 | {(S)-3-[(6-Chloro-quinoxalin-2-ylamino)-methyl)-pyrrolidin-1-yl}-(5-phenyl-isoxazol-4-yl)-methanone | (6-Chloro-quinoxalin-2-yl)-(R)-1-pyrrolidin-3-ylmethyl-amine (intermediate 4) and 4-phenyl-isoxazole-5-carboxylic acid (commercially available) | 434.2 |
| 31 | 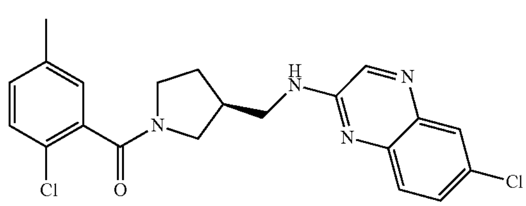 | (2-Chloro-5-methyl-phenyl)-{(S)-3-[(6-chloro-quinoxalin-2-ylamino)-methyl]-pyrrolidin-1-yl}-methanone | (6-Chloro-quinoxalin-2-yl)-(R)-1-pyrrolidin-3-ylmethyl-amine (intermediate 4) and 2-chloro-5-methyl-benzoic acid (commercially available) | 415.2 |
| 32 | 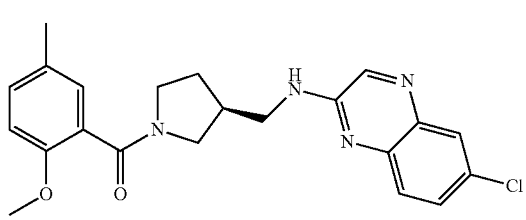 | {(S)-3-[(6-Chloro-quinoxalin-2-ylamino)-methyl]-pyrrolidin-1-yl}-(2-methoxy-5-methyl-phenyl)-methanone | (6-Chloro-quinoxalin-2-yl)-(R)-1-pyrrolidin-3-ylmethyl-amine (intermediate 4) and 2-methoxy-5-methyl-benzoic acid (commercially available) | 411.2 |

The invention claimed is:
1. A compound of formula I

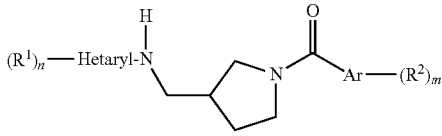

wherein
R¹ is halogen;
R² is halogen, lower alkyl, lower alkoxy, lower alkyl substituted by halogen, lower alkoxy substituted by halogen or phenyl;
Hetaryl is

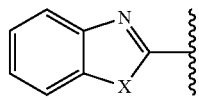

X is S;
Ar is aryl or heteroaryl;
n is 0, 1 or 2; and
m is 0, 1 or 2;
or a pharmaceutically suitable acid addition salt, optically pure enantiomer, racemate or diastereomeric mixture thereof.

2. The compound of claim 1, wherein R² is lower alkyl, lower alkoxy, lower alkoxy substituted by halogen or phenyl.

3. The compound of claim 2, wherein R² is methyl, methoxy, 1,1,2,2-tetrafluoro-ethoxy or phenyl.

4. The compound of claim 1, wherein R¹ is chloro or fluoro.

5. The compound of claim 1, wherein n is 1.

6. The compound of claim 1, selected from the group consisting of
{(S)-3-[(6-fluoro-benzothiazol-2-ylamino)-methyl]-pyrrolidin-1-yl}-(2-trifluoromethyl-phenyl)-methanone;
{(S)-3-[(6-fluoro-benzothiazol-2-ylamino)-methyl]-pyrrolidin-1-yl}-(2-trifluoromethoxy-phenyl)-methanone;
{(S)-3-[(6-fluoro-benzothiazol-2-ylamino)-methyl]-pyrrolidin-1-yl}-[2-(1,1,2,2-tetrafluoro-ethoxy)-phenyl]-methanone;
{(S)-3-[(6-fluoro-benzothiazol-2-ylamino)-methyl]-pyrrolidin-1-yl}-(5-methyl-2-trifluoromethyl-phenyl)-methanone;
{(S)-3-[(6-fluoro-benzothiazol-2-ylamino)-methyl]-pyrrolidin-1-yl}-(5-methyl-3-phenyl-isoxazol-4-yl)-methanone;
{(S)-3-[(6-fluoro-benzothiazol-2-ylamino)-methyl]-pyrrolidin-1-yl}-(5-phenyl-isoxazol-4-yl)-methanone;
(2-chloro-5-methyl-phenyl)-{(S)-3-[(6-fluoro-benzothiazol-2-ylamino)-methyl]-pyrrolidin-1-yl}-methanone; and
{(S)-3-[(6-fluoro-benzothiazol-2-ylamino)-methyl]-pyrrolidin-1-yl}-(2-methoxy-5-methyl-phenyl)-methanone.

7. The compound of claim 1, selected from the group consisting of
{(S)-3-[(6-Fluoro-benzothiazol-2-ylamino)-methyl]-pyrrolidin-1-yl}-[2-(1,1,2,2-tetrafluoro-ethoxy)-phenyl]-methanone;
{(S)-3-[(6-Fluoro-benzothiazol-2-ylamino)-methyl]-pyrrolidin-1-yl}-(5-methyl-3-phenyl-isoxazol-4-yl)-methanone; and
{(S)-3-[(6-Fluoro-benzothiazol-2-ylamino)-methyl]-pyrrolidin-1-yl}-(5-phenyl-isoxazol-4-yl)-methanone.

8. A pharmaceutical composition comprising a compound of formula I

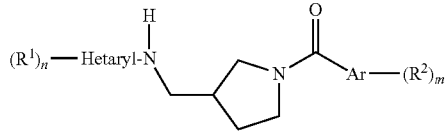

wherein
R¹ is halogen;
R² is halogen, lower alkyl, lower alkoxy, lower alkyl substituted by halogen, lower alkoxy substituted by halogen or phenyl;
Hetaryl is

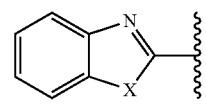

X is S;
Ar is aryl or heteroaryl;
n is 0, 1 or 2; and
m is 0, 1 or 2;
or a pharmaceutically suitable acid addition salt, optically pure enantiomer, racemate or diastereomeric mixture thereof and a pharmaceutically acceptable carrier.

* * * * *